(12) United States Patent
Koshiyama et al.

(10) Patent No.: US 11,732,236 B2
(45) Date of Patent: Aug. 22, 2023

(54) METHOD FOR PRODUCING NOVEL MICROORGANISMS AND ERGOTHIONEINE

(71) Applicants: Kureha Corporation, Tokyo (JP); National Institute Of Advanced Industrial Science And Technology, Tokyo (JP)

(72) Inventors: Tatsuyuki Koshiyama, Tokyo (JP); Mutsumi Kaneko, Tokyo (JP); Yukihiro Higashiyama, Tokyo (JP); Shun Sato, Ibaraki (JP); Tomotake Morita, Ibaraki (JP); Azusa Saika, Ibaraki (JP)

(73) Assignees: KUREHA CORPORATION, Tokyo (JP); NATIONAL INSTITUTE OF ADVANCED INDUSTRIAL SCIENCE AND TECHNOLOGY, Tokyo (JP)

( * ) Notice: Subject to any disclaimer, the term of this patent is extended or adjusted under 35 U.S.C. 154(b) by 0 days.

(21) Appl. No.: 17/758,329

(22) PCT Filed: Aug. 6, 2020

(86) PCT No.: PCT/JP2020/030145
§ 371 (c)(1),
(2) Date: Jul. 1, 2022

(87) PCT Pub. No.: WO2021/140693
PCT Pub. Date: Jul. 15, 2021

(65) Prior Publication Data
US 2023/0043773 A1 Feb. 9, 2023

(30) Foreign Application Priority Data

Jan. 9, 2020 (JP) .................................. 2020-002301

(51) Int. Cl.
*C12N 1/16* (2006.01)
*C12P 13/04* (2006.01)
*C12R 1/645* (2006.01)

(52) U.S. Cl.
CPC .............. *C12N 1/165* (2021.05); *C12P 13/04* (2013.01); *C12N 2500/34* (2013.01); *C12R 2001/645* (2021.05)

(58) Field of Classification Search
CPC ......... C12N 1/165; C12N 1/145; C12P 13/04; C12R 2001/645
See application file for complete search history.

(56) References Cited

U.S. PATENT DOCUMENTS

| | | |
|---|---|---|
| 10,760,107 B2 | 9/2020 | Hara et al. |
| 2014/0121156 A1 | 5/2014 | Hausman |
| 2017/0321235 A1 | 11/2017 | Hara et al. |
| 2020/0140904 A1 | 5/2020 | Maeda et al. |
| 2021/0164004 A1 | 6/2021 | Tani |
| 2022/0056494 A1 | 2/2022 | Wei et al. |

FOREIGN PATENT DOCUMENTS

| | | |
|---|---|---|
| CN | 109439553 A | 3/2019 |
| CN | 110283856 A | 9/2019 |
| EP | 3 252 142 A1 | 12/2017 |
| JP | 2009-249356 A | 10/2009 |
| WO | WO 2012/174035 A2 | 12/2012 |
| WO | 2016/104437 A1 | 6/2016 |
| WO | 2016/121285 A1 | 8/2016 |
| WO | 2019/004234 A1 | 1/2019 |

OTHER PUBLICATIONS

Fujitani, Y. et al., "Ergothioneine production using methylobacterium species, yeast, and fungi", Journal of Bioscience and Bioengineering, 2018, vol. 12 6, No. 6, pp. 715-722, pp. 717, 718.
Takusagawa, et al., "Ergothioneine production with Aspergillus oryzae" Bioscience, Biotechnology, and Biochemistry, 2019, vol. 83, No. 1, 181-184; https://doi.org/10.1080/09168451.2018.152721083.
Shin-Yi Lin, et al., "Submerged Cultivation of Mycelium with High Ergothioneine Content from the Culinary-Medicinal Golden Oyster Mushroom, *Pleurotus citrinopileatus* (Higher Basidiomycetes)", International Journal of Medicinal Mushrooms, 17(8): 749-761 (2015).
Australian Office Action for Australian Application No. 2020420098, dated Jul. 28, 2022.
International Preliminary Report on Patentability and English translation of the Written Opinion of the International Searching Authority for International Application No. PCT/JP2020/030145, dated Jul. 12, 2022.
Office Action dated Oct. 6, 2022, in Canadian Patent Application No. 3,163,427.
Office Action dated Nov. 14, 2022, in Eurasian Patent Application No. 202291571.
Office Action dated Aug. 17, 2022, in Republic of Korea Patent Application No. 10-2022-7022701.
Chinese Office Action and Search Report for Chinese Application No. 202080085536.1, dated Nov. 14, 2022, with an English translation.
Liu et al, "Biosynthesis and Catabolism of L-Ergothioneine", Natural Product Research and Development, vol. 27, 2015, pp. 1112-1117, with an English translation.
Eurasian Office Action for Eurasian Application No. 202291571, dated Feb. 12, 2023, with English translation.
Office Action dated Mar. 13, 2023, in Brazilian Patent Application No. BR112022013285-9.

*Primary Examiner* — Lynn Y Fan
(74) *Attorney, Agent, or Firm* — Birch, Stewart, Kolasch & Birch, LLP (57) ABSTRACT

A microorganism of the present invention is *Dirkmeia churashimaensis* (NITE BP-03054), *Papiliotrema flavescens* (NITE BP-03051), *Papiliotrema flavescens* (NITE BP-03052), or *Apiotrichum porosum* (NITE BP-03053).

2 Claims, 2 Drawing Sheets

METHOD FOR PRODUCING NOVEL MICROORGANISMS AND ERGOTHIONEINE

TECHNICAL FIELD

The present invention relates to a novel microorganism and a method for producing ergothioneine by culturing the novel microorganism to obtain ergothioneine.

BACKGROUND ART

Ergothioneine is one of sulfur-containing amino acids. Ergothioneine has a higher antioxidant effect than that of vitamin E, and has been attracted attention as a highly useful compound in the fields of health, beauty and the like.

For example, Patent Document 1 and Non-Patent Document 1 describe transformed filamentous fungi with enhanced ergothioneine production capability.

Non-Patent Document 2 describes a transformed microorganism of the genus *Methylobacrium* with enhanced ergothioneine production capability. Non-Patent Document 2 describes that microorganisms of the genera *Aureobasidium* and *Rhodotorula* have ergothioneine production capability.

Non-Patent Document 3 describes that a microorganism of the genus *Pleurotus* has ergothioneine production capability.

CITATION LIST

Patent Document

Patent Document 1: WO 2016/121285

Non-Patent Literature

Non-Patent Document 1: S. Takusagawa, Biosci. Biotechnol. Biochem., 83, 181-184 (2019)
Non-Patent Document 2: Y. Fujitani et al., J. Biosci. Bioeng., 126, 715-722 (2018)
Non-Patent Document 3: S Y. Lin, Int. J. Med. Mushrooms, 17, 749-761 (2015)

SUMMARY OF INVENTION

Technical Problem

It is known that ergothioneine is not biosynthesized in the human body, but biosynthesized in some microorganisms. Thus, research and development on microorganisms that produce ergothioneine and modification of microorganisms to enhance the ergothioneine production are in progress, as described in the prior art documents. However, the microorganisms described in the prior art documents have a low ergothioneine production, and search and development on microorganisms having a high ergothioneine production are desired.

Gene recombination techniques can be used to modify microorganisms to enhance the ergothioneine production. However, the ergothioneine produced by the microorganisms cannot be used in the food industry or the like. Accordingly, there is a strong desire to search for microorganisms with high ergothioneine production, which have not been subjected to gene recombination and are unmodified.

The present invention has been made in light of the above problem, and an object thereof is to provide a novel microorganism with high ergothioneine production.

Solution to Problem

As a result of screening, the present inventors have found a novel microorganism that has higher ergothioneine production than that of known microorganisms, and completed the present invention.

The microorganism according to the present invention is a microorganism belonging to *Dirkmeia churashimaensis* (NITE BP-03054), a microorganism belonging to *Papiliotrema flavescens* (NITE BP-03051), a microorganism belonging to *Papiliotrema flavescens* (NITE BP-03052), or a microorganism belonging to *Apiotrichum porosum* (NITE BP-03053).

Advantageous Effects of Invention

According to one aspect of the present invention, a microorganism having high ergothioneine production can be provided.

DESCRIPTION OF EMBODIMENTS

The microorganism of the present embodiment is a microorganism belonging to the genus *Dirkmeia* capable of producing ergothioneine, a microorganism belonging to the genus *Papiliotrema* capable of producing ergothioneine, or a microorganism belonging to the genus *Apiotrichum* capable of producing ergothioneine.

The microorganism of the present embodiment has high ergothioneine production. Ergothioneine is one of sulfur-containing amino acids and has excellent antioxidant effect. In addition, the microorganism of the present embodiment has not been modified by the gene recombination technique or the like, and thus can also be used in the food industry.

Hereinafter, the microorganism of the present embodiment will be described in detail.

[1. *Dirkmeia churashimaensis* S111]

*Dirkmeia churashimaensis* S111 (hereinafter abbreviated as "yeast S111" in some cases) is a microorganism that is first isolated using, as an isolation source, leaves (young leaves) collected in Tsukuba-shi, Ibaraki.

The base sequences of the ribosomal RNA gene 26S rDNA-D1/D2 and ITS regions were determined. Homology search by BLAST was performed across the TechnoSuruga Laboratory microorganism identification system (TechnoSuruga Laboratory, Japan) database DB-FU10.0 and the International Nucleotide Sequence Databases (DDBJ/ENA (EMBL)/GenBank). As a result, yeast S111 was attributed to *Dirkmeia churashimaensis*. Also, as illustrated in the Examples, yeast S111 exhibits almost similar physiological/biochemical properties to those of *Dirkmeia churashimaensis*, except that differences were observed in terms of the assimilation of erythritol and succinates as carbon sources and nitrates as nitrogen sources and the viability at 37° C.

Yeast S111 was deposited at the NITE Patent Microorganisms Depositary (NPMD), National Institute of Technology and Evaluation (hereinafter abbreviated as "NITE")

(#122, 2-5-8 Kazusakamatari, Kisarazu-shi, Chiba, Japan) (date of original deposition: Oct. 25, 2019, Accession No.: NITE BP-03054).

The method for culturing yeast S111 may be performed in accordance with common culture methods for microorganisms of the genus *Dirkmeia*. The culture form is batchwise culture using a liquid medium or fed-batch culture in which a carbon source and/or an organic nitrogen source is continuously added to the culture system, and aeration agitation is desirably performed. As the medium, a medium containing carbon and nitrogen sources that are assimilable by microorganisms belonging to the genus *Dirkmeia* or a required nutrient source such as an inorganic salt may be used. The pH for culture is preferably from 3 to 8, the culture temperature is preferably 20° C. to 37° C., and the incubation time is preferably from 2 to 14 days.

[2. *Papiliotrema flavescens* EA071]

*Papiliotrema flavescens* EA071 (hereinafter abbreviated as "yeast EA071" in some cases) is a microorganism that is first isolated using, as an isolation source, leaves of Japanese pampas grass collected around Lake Motosu.

The base sequences of the ribosomal RNA gene 26S rDNA-D1/D2 and ITS regions were determined. Homology search by BLAST was performed across the TechnoSuruga Laboratory microorganism identification system (TechnoSuruga Laboratory, Japan) database DB-FU10.0 and the International Nucleotide Sequence Databases (DDBJ/ENA (EMBL)/GenBank). As a result, yeast EA071 was attributed to *Papiliotrema flavescens*. Also, as illustrated in the Examples, yeast EA071 exhibits almost similar physiological/biochemical properties to those of *Papiliotrema flavescens* except that differences were observed in terms of inulin and water-soluble starch as carbon sources.

Yeast EA071 was deposited at the NITE Patent Microorganisms Depositary (NPMD), National Institute of Technology and Evaluation (NITE) (#122, 2-5-8 Kazusakamatari, Kisarazu-shi, Chiba, Japan) (date of original deposition: Oct. 25, 2019, Accession No.: NITE BP-03051).

The method for culturing yeast EA071 may be performed in accordance with common culture methods for microorganisms of the genus *Papiliotrema*. The culture form is batchwise culture using a liquid medium or fed-batch culture in which a carbon source and/or an organic nitrogen source is continuously added to the culture system, and aeration agitation is desirably performed. As the medium, a medium containing carbon and nitrogen sources that are assimilable by microorganisms belonging to the genus *Papiliotrema* or a required nutrient source such as an inorganic salt may be used. The pH for culture is preferably from 3 to 8, the culture temperature is preferably 20° C. to 30° C., and the incubation time is preferably from 2 to 14 days.

[3. *Papiliotrema flavescens* EA361]

*Papiliotrema flavescens* EA361 (hereinafter abbreviated as "yeast EA361" in some cases) is a microorganism that is first isolated using, as an isolation source, the bark collected around Lake Suwa.

The base sequences of the ribosomal RNA gene 26S rDNA-D1/D2 and ITS regions were determined. Homology search by BLAST was performed across the TechnoSuruga Laboratory microorganism identification system (TechnoSuruga Laboratory, Japan) database DB-FU10.0 and the International Nucleotide Sequence Databases (DDBJ/ENA (EMBL)/GenBank). As a result, yeast EA361 was attributed to *Papiliotrema flavescens*. Also, as illustrated in the Examples, yeast EA071 exhibits almost similar physiological/biochemical properties to those of *Papiliotrema flavescens* except that differences were observed in terms of inulin and water-soluble starch as carbon sources.

Yeast EA361 was deposited at the NITE Patent Microorganisms Depositary (NPMD), National Institute of Technology and Evaluation (NITE) (#122, 2-5-8 Kazusakamatari, Kisarazu-shi, Chiba, Japan) (date of original deposition: Oct. 25, 2019, Accession No.: NITE BP-03052).

The method for culturing yeast EA361 may be performed in accordance with common culture methods for microorganisms of the genus *Papiliotrema*. The culture form is batchwise culture using a liquid medium or fed-batch culture in which a carbon source and/or an organic nitrogen source is continuously added to the culture system, and aeration agitation is desirably performed. As the medium, a medium containing carbon and nitrogen sources that are assimilable by microorganisms belonging to the genus *Papiliotrema* or a required nutrient source such as an inorganic salt may be used. The pH for culture is preferably from 3 to 8, the culture temperature is preferably 20° C. to 30° C., and the incubation time is preferably from 2 to 14 days.

[4. *Apiotrichum porosum* EA702]

*Apiotrichum porosum* EA702 (hereafter abbreviated as "yeast EA702" in some cases) is a microorganism that is first isolated using, as an isolation source, from soil collected in Iwaki-shi.

The base sequences of the ribosomal RNA gene 26S rDNA-D1/D2 and ITS regions were determined. Homology search by BLAST was performed across the TechnoSuruga Laboratory microorganism identification system (TechnoSuruga Laboratory, Japan) database DB-FU10.0 and the International Nucleotide Sequence Databases (DDBJ/ENA (EMBL)/GenBank). As a result, yeast EA702 was attributed to *Apiotrichum porosum*. Also, as illustrated in the Examples, yeast EA702 exhibits almost similar physiological/biochemical properties to those of *Papiliotrema flavescens* except that differences were observed in terms of inulin as a carbon source and 50% D-glucose in the resistance test.

Yeast EA702 was deposited at the NITE Patent Microorganisms Depositary (NPMD), National Institute of Technology and Evaluation (NITE) (#122, 2-5-8 Kazusakamatari, Kisarazu-shi, Chiba, Japan) (date of original deposition: Oct. 25, 2019, Accession No.: NITE BP-03053).

The method for culturing yeast EA702 may be performed in accordance with common culture methods for microorganisms of the genus *Apiotrichum*.

The culture form is batchwise culture using a liquid medium or fed-batch culture in which a carbon source and/or an organic nitrogen source is continuously added to the culture system, and aeration agitation is desirably performed. As the medium, a medium containing carbon and nitrogen sources that are assimilable by microorganisms belonging to the genus *Apiotrichum* or a required nutrient source such as an inorganic salt may be used. The pH for culture is preferably from 3 to 8, the culture temperature is preferably 20° C. to 27° C., and the incubation time is preferably from 2 to 14 days.

[Method for Producing Ergothioneine]

The method for producing ergothioneine of the present embodiment includes culturing the microorganism described above to obtain a culture containing ergothioneine.

Collection of ergothioneine from the culture containing ergothioneine may be accomplished, for example, by a common method for collecting and purifying ergothioneine from a microorganism culture. The culture includes, for example, a culture supernatant, cultured microbial cells, and a crushed product of cultured microbial cells. For example, the cultured microbial cells are collected by centrifugation or the like of the culture. The collected microbial cells are subjected to hot water extraction or the like to obtain an extract liquid containing ergothioneine. Ergothioneine can then be collected by purifying the extract liquid. The ergothioneine production of the microorganism can be quantified, for example, by measuring the resulting extract liquid using a high performance liquid chromatography instrument and a mass spectrometer such as LCMS.

SUMMARY

The microorganism according to the present embodiment is a microorganism belonging to *Dirkmeia churashimaensis* (NITE BP-03054), a microorganism belonging to *Papiliotrema flavescens* (NITE BP-03051), a microorganism belonging to *Papiliotrema flavescens* (NITE BP-03052), or a microorganism belonging to *Apiotrichum porosum* (NITE BP-03053).

Also, the method for producing ergothioneine according to the present embodiment includes culturing the microorganism described above to obtain a culture containing ergothioneine.

Embodiments of the present invention will be described in further detail hereinafter using examples. The present invention is not limited to the examples below, and it goes without saying that various aspects are possible with regard to the details thereof. Furthermore, the present invention is not limited to the embodiments described above, and various modifications are possible within the scope indicated in the claims. Embodiments obtained by appropriately combining the technical means disclosed by the embodiments are also included in the technical scope of the present invention. In addition, all of the documents described in the present specification are herein incorporated by reference.

EXAMPLES

In the following Examples, the symbol "%" represents % by mass, unless otherwise indicated.

(1) Enrichment Culture Using Isolation Source Collected from Environment

First, microorganism sampling from environments such as plants and soil was performed in two stages. As a result, a total of 113 samples (30 samples for the first stage and 83 samples for the second stage) were collected.

Then, the samples collected were each immersed in a 15-mL plastic tube containing 2 mL of a screening medium, and cultured at 200 rpm and 25° C. for 3 to 5 days. The screening medium used was a YM medium containing an antibiotic. Specifically, a medium containing 1% glucose, 0.5% peptone, 0.3% yeast extract, 0.3% malt extract, 0.01% streptomycin sulfate, and 0.005% chloramphenicol was used.

Then, 111 samples (30 samples for the first stage and 81 samples for the second stage) in which the medium was visually observed to be cloudy (microorganisms proliferated) were selected.

(2) Selection of Samples with Oxidative Stress Load

Culture solutions of the 111 samples selected in (1) above were each diluted 100 or 100000 times in a YM medium. The diluted culture solution was applied to a YM agar medium and a YM agar medium added with 3 mM $H_2O_2$ (hereinafter abbreviated as $H_2O_2$-containing YM agar medium), and cultured at 25° C. for 2 to 5 days.

The number of colonies having grown on the YM agar medium and the number of colonies having grown on the $H_2O_2$-containing YM agar medium were counted. Then, 83 samples in which colonies had grown on both the YM agar medium and the $H_2O_2$-containing YM agar medium were selected.

In addition, for the colonies having grown on the agar medium in the selected 83 samples, the morphology and color were visually observed, and 164 yeast-like colonies of different types (51 colonies for the first stage and 113 colonies for the second stage) were selected.

(3) Culture of Selected Colonies in 96 Wells

The 164 colonies selected in (2) above were inoculated into 96 well plates containing 1 mL of a YM medium, and cultured at 1600 rpm and 25° C. for 3 to 4 days. After culturing, the collected culture solutions were centrifuged at 2000 rpm and 4° C. for 10 minutes. The cell pellets obtained by centrifugation were washed with pure 1 mL and centrifuged again.

To the cell pellets obtained by centrifugation, 0.1 mL of pure water was added to suspend the pellets therein. The resulting suspensions were heated at 96° C. for 10 minutes to extract the intracellular components. The extracted intracellular components were then centrifuged to remove microbial cell residues, thereby obtaining extract liquids.

(4) Quantitative Analysis of Ergothioneine in Extract Liquid by LCMS

A mixed solution of 0.15 mL of each of the extract liquids obtained in (3) above and 0.35 mL of acetonitrile was filtered through a 0.45-μm PVDF filter. The resulting filtrate was used as a sample for LCMS measurement.

LCMS-2020, available from Shimadzu Corporation, was used for LCMS analysis. In addition, an Asahipak NH2P-40 2D+ guard column, available from SHODEX, was used as the column for LC. A mixed solution of 10 mM ammonium formate and acetonitrile (10 mM ammonium formate/acetonitrile=30/70 (v/v)) was used as the mobile phase for LC. The flow rate was set to 0.1 mL/min, and analysis was performed at 25° C.

In MS detection, ionization was performed in DUIS mode for performing ESI ionization and APCI ionization simultaneously. Detection was also performed in SIM mode of m/z=230 (+) in which ergothioneine could be detected.

As a result of analyzing the extract liquids of the 164 colonies selected in (2) above, 14 colonies with high ergothioneine production (5 colonies for the first stage and 9 colonies for the second stage) were selected.

Figure 1:
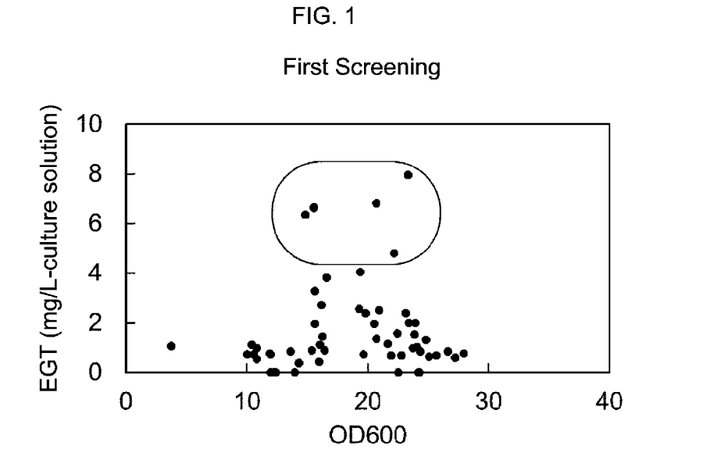
FIG. 1 is a graph showing results of first screening.
Figure 2:
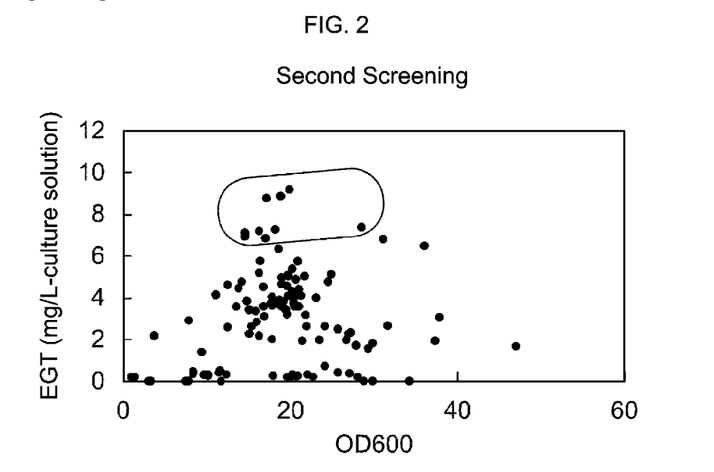
FIG. 2 is a graph showing results of second screening.

Also, FIGS. 1 and 2 are graphs showing the amounts of ergothioneine produced by the microorganism samples collected at the first and second stages of microorganism sampling, respectively. The horizontal axis in FIGS. 1 and 2 shows the values obtained by measuring the culture solutions obtained after culture in (3) above at OD600. The vertical axis shows the amounts of ergothioneine (mg/L (culture solution)) in the culture solutions obtained after culture in (3) above. The amount of ergothioneine is a value obtained by LCMS analysis. In FIGS. 1 and 2, the 14 colonies selected are enclosed in a circle.

(5) Scale-Up Culture of Ergothioneine-Producing Microorganism in Flask

The 14 colonies selected in (4) above were each inoculated into a 300-mL flask containing 50 mL of a YM medium, and cultured at 200 rpm and 25° C. for 7 days (n=1).

The culture solutions on Days 3 to 7 were collected as appropriate. As in (3) above, after centrifugation and washing of the microbial cells, extract liquids were collected by hot water extraction.

The resulting extract liquids were analyzed by LCMS in a similar manner as in (4) above to select five strains (S111, EA071, EA361, EA701, and EA702) with high ergothioneine production.

Colonies of the selected five strains were each inoculated into a 300-mL flask containing 50 mL of a YM medium, and cultured at 200 rpm and 25° C. for 5 days (n=3). The ergothioneine productions on Days 3 and 5 of culture were then measured by LCMS. The ergothioneine productions of the colonies of the selected five strains are shown in FIG. 3.

Figure 3:
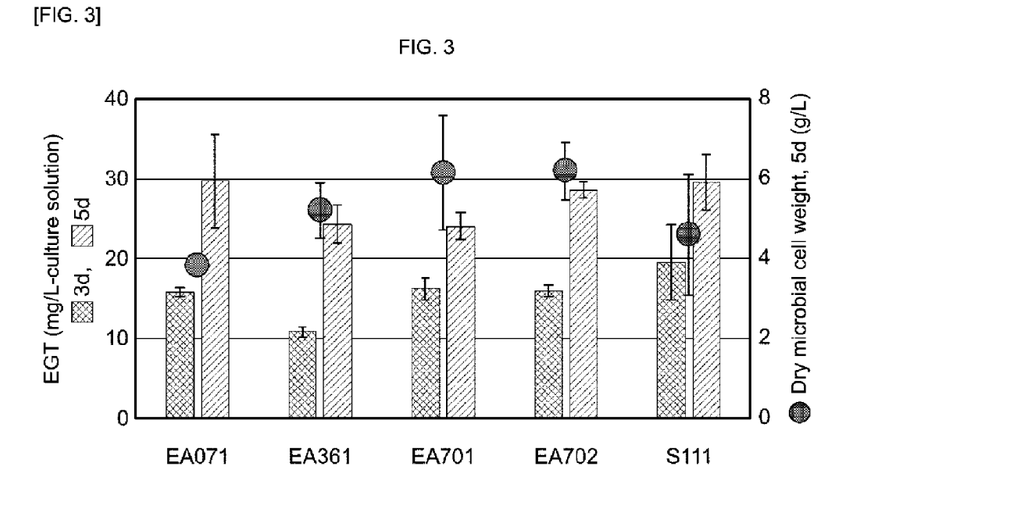
FIG. 3 is a graph showing evaluation results of the ergothioneine production of five novel microorganism strains.

In FIG. 3, the left bar graph for each of the strains indicates the ergothioneine production on Day 3 of culture. The right bar graph for each of the strains indicates the ergothioneine production on Day 5 of culture.

(7) Identification of Selected Five Strains

Estimation of the classification groups to which the selected five strains were attributed was performed by analysis of the base sequences of the ribosomal RNA gene 26S rDNA-D1/D2 and ITS regions.

As a result of analysis of the base sequences, it was estimated that the S111 strain belongs to *Dirkmeia churashimaensis*; that the EA071 and EA361 strains belong to *Papiliotrema flavescens*, and that the EA701 and EA702 strains belong to *Apiotrichum porosum*.

Table 1 shows the ergothioneine (EGT) productions and production rates of the selected five strains. Table 2 shows the productions and production rates of known microorganisms. In Tables 1 and 2, unless otherwise noted, the unit for the ergothioneine (EGT) production is mg/L, and the unit for the EGT production rate is mg/L/d (ergothioneine production per day). Also, the EGT productions in Table 1 indicate the ergothioneine productions on Day 5 of culture.

TABLE 1

| | Name of strain | Putative microorganism | EGT Production | EGT production rate |
|---|---|---|---|---|
| First sampling | S111 | Dirkmeia churashimaensis | 29.5 ± 3.5 | 5.9 |
| Second sampling | EA071 | Papiliotrema flavescens | 29.7 ± 5.7 | 5.9 |
| | EA361 | | 24.3 ± 2.4 | 4.9 |
| | EA701 | Apiotrichum porosum | 24.1 ± 1.6 | 4.8 |
| | EA702 | | 28.7 ± 1.0 | 5.7 |

TABLE 2

| Microorganism | EGT Production | EGT production rate | Reference |
|---|---|---|---|
| *Aureobasidium pullulans* kz25 | 14 | 2 | J Biosci Bioeng 126 (2018) 715 |
| *Rhodotorula mucilaginosa* 241c | 24 | 3.4 | J Biosci Bioeng 126 (2018) 715 |
| *Aspergillus sojae* | 15 | 5 | WO2016/121285 |
| *Aspergillus oryzae* NSAR1 | 11.5 (mg/kg) | 2.3 (mg/kg/d) | Biosci Biotechnol Biochem 83 (2019) 181 |
| *Pleurotus citrinopileatus* | 13-98 | 0.8-6.1 | I J Med Mushroom 17 (2015) 749 |
| *Methylobacterium aquaticum* 22A | 12.2 | 1.7 | J Biosci Bioeng 126 (2018) 715 |

It was found, from Tables 1 and 2, that the ergothioneine productions of the selected five strains were equal to or higher than the ergothioneine productions of the known ergothioneine-producing microorganisms. It was also found that the ergothioneine production rates of the selected five strains were also equal to or higher than the production rates of the known ergothioneine-producing microorganisms.

(8) Molecular Phylogenetic Position and Physiological Properties of S111 Strain

For the base sequences of the 26S rDNA-D1/D2 regions and ITS-5.8 rDNA in the S111 strain, homology search by BLAST was performed across the International Nucleotide Sequence Databases. As a result, the base sequences exhibited from 98.4 to 100% homology with a plurality of base sequences of *Dirkmeia churashimaensis* as one type of basidiomycetous yeast. In the molecular phylogenetic tree analyzed based on the obtained base sequences, the S111 strain showed the same molecular phylogenetic position as those of the plurality of base sequences of *Dirkmeia churashimaensis*.

The S111 strain was cultured on a YM agar plate medium at 27° C. for 7 days, and the colonies formed were observed. The shape of the margin of the colonies was entire, and the raised state thereof was flat and wrinkled. The shape of the surface of the colonies was smooth. In addition, the colonies were dull and butter-like, and light orange to cream-colored.

Further, the S111 strain was cultured on a YM agar plate medium at 27° C. for 7 days, and then the cell morphological properties thereof were also observed. It was seen that the nutritive cells were oval to ovoid in shape, and that the strain was proliferated through budding. No formation of sexual reproductive organs was observed in the plate 4 weeks or longer after the start of culture.

The morphological properties of the S111 strain described above nearly matched the characteristics of *Dirkmeia churashimaensis* to which it was attributed according to the DNA sequence analysis of the D1/D2 and ITS regions. The physiological properties of the S111 strains are shown in Table 3.

In Table 3, the symbol "+" indicates positive. The symbol "−" indicates negative. The letter "W" indicates weakly positive. The letter "D" indicates gradually becoming positive over a period of 1 week or longer after the start of the test, and the letter "L" indicates rapidly becoming positive 2 weeks or longer after the start of the test.

TABLE 3

| <Saccharide fermentation test> | | | | | |
|---|---|---|---|---|---|
| Glucose | − | | | | |
| <Carbon source assimilation test> | | | | | |
| Glucose | + | Maltose | + | Ribitol (adonitol) | + |
| Galactose | + | α-methyl-D-glucoside | + | D-mannitol | + |
| L-sorbose | + | Cellobiose | + | Inositol | L |
| D-glucosamine | + | Salicin | D | 2-keto-D-gluconate | + |
| D-ribose | L | Melibiose | + | DL-lactate | + |
| D-xylose | + | Lactose | + | Succinate | W |
| D-arabinose | + | Water soluble starch | + | Ethanol | + |
| L-rhamnose | + | Glycerol | + | Saccharate | − |
| Sucrose | + | Erythritol | + | N-acetyl-D-glucosamine | + |
| <Nitrogen source assimilation test> | | | | | |
| Nitrate | + | Nitrite | D | Ethylamine | + |
| <Resistance test> | | | | | |
| Viability at 25° C. | + | Viability at 30° C. | + | Viability at 37° C. | + |
| 0.01% Cycloheximide | D | 50% (w/v) D-glucose | + | 10% NaCl/5% glucose | + |
| <Vitamin requirement test> | | | | | |
| Vitamin-free medium | + | | | | |

Through the measurements of the molecular phylogenetic position and physiological properties as well as the ergothioneine production, the S111 strain was determined to be a novel microorganism attributed to *Dirkmeia churashimaensis*.

(9) Molecular Phylogenetic Position and Physiological Properties of EA071 Strain For the base sequences of the 26S rDNA-D1/D2 regions and ITS-5.8 rDNA in the EA071 strain, homology search by BLAST was performed across the International Nucleotide Sequence Databases. As a result, the base sequences exhibited from 99.4 to 100% homology with a plurality of base sequences of *Cryptococcus flavescens* (current name: *Papiliotrema flavescens*) as one type of basidiomycetous yeast. In the molecular phylogenetic tree analyzed based on the obtained base sequences, the EA071 strain was included in the phyletic group composed of the genus *Papiliotrema*. Then, the strain showed the same molecular phylogenetic position as that of *Cryptococcus flavescens* (current name: *Papiliotrema flavescens*) CBS942$^T$.

The EA071 strain was cultured on a YM agar plate medium at 27° C. for 7 days, and the colonies formed were observed. The shape of the margin of the colonies was entire, and the raised state thereof was cushion-shaped. The shape of the surface of the colonies was smooth. In addition, the colonies were luminous and viscous, and cream-colored.

Further, the EA071 strain was cultured on a YM agar plate medium at 27° C. for 7 days, and then the cell morphological properties thereof were also observed. It was seen that the nutritive cells were subglobular to oval in shape, and that the strain was proliferated through budding. No formation of sexual reproductive organs was observed in the plate 4 weeks or longer after the start of culture.

The morphological properties of the EA071 strain described above nearly matched the characteristics of *Papiliotrema flavescens* to which it was attributed by the DNA sequence analysis of the D1/D2 and ITS regions. The physiological properties of the EA071 strains are shown in Table 4.

TABLE 4

| <Saccharide fermentation test> | | | | | |
|---|---|---|---|---|---|
| Glucose | − | | | | |
| <Carbon source assimilation test> | | | | | |
| Glucose | + | Cellobiose | + | D-mannitol | + |
| Galactose | + | Salicin | + | Galactitol (dulcitol) | + |
| L-sorbose | − | Melibiose | + | Inositol | W |
| D-glucosamine | − | Lactose | + | 2-keto-D-gluconate | + |
| D-ribose | + | Raffinose | + | D-gluconate | + |
| D-xylose | + | Melezitose | + | D-glucuronate | + |
| L-arabinose | + | Inulin | + | DL-lactate | D |
| D-arabinose | W | Water soluble starch | + | Succinate | W |
| L-rhamnose | + | Glycerol | D | Methanol | − |
| Sucrose | + | Erythritol | L | Ethanol | + |

TABLE 4-continued

| | | | | | |
|---|---|---|---|---|---|
| Maltose | + | Ribitol (adonitol) | + | N-acetyl-D-glucosamine | − |
| Trehalose | + | D-glucitol (sorbitol) | + | Hexadecane | − |
| α-methyl-D-glucoside | + | | | | |
| <Nitrogen source assimilation test> | | | | | |
| Nitrate | − | Creatinine | − | | |
| <Resistance test> | | | | | |
| Viability at 30° C. | + | Viability at 37° C. | − | | |
| 0.01% Cycloheximide | + | 50% (w/v) D-glucose | + | 10%NaCl/5% glucose | − |
| <Vitamin requirement test> | | | | | |
| Vitamin-free medium | + | | | | |

Through the measurements of the molecular phylogenetic position and physiological properties as well as the ergothioneine production, the EA071 strain was determined to be a novel microorganism attributed to *Papiliotrema flavescens*.

(10) Molecular Phylogenetic Position and Physiological Properties of EA361 Strain For the base sequences of the 26S rDNA-D1/D2 regions and ITS-5.8 rDNA in the EA361 strain, homology search by BLAST was performed across the International Nucleotide Sequence Databases. As a result, the base sequences exhibited from 99.4 to 100% homology with a plurality of base sequences of *Cryptococcus flavescens* (current name: *Papiliotrema flavescens*) as one type of basidiomycetous yeast. In the molecular phylogenetic tree analyzed based on the obtained base sequences, the EA361 strain was included in the phyletic group composed of the genus *Papiliotrema*. Then, the strain showed the same molecular phylogenetic position as that of *Cryptococcus flavescens* (current name: *Papiliotrema flavescens*) CBS942T.

The EA361 strain was cultured on a YM agar plate medium at 27° C. for 7 days, and the colonies formed were observed. The shape of the margin of the colonies was entire, and the raised state thereof was cushion-shaped. The shape of the surface of the colonies was smooth. In addition, the colonies were luminous and viscous, and cream-colored.

Further, the EA361 strain was cultured on a YM agar plate medium at 27° C. for 7 days, and then the cell morphological properties thereof were also observed. It was seen that the nutritive cells were subglobular to oval in shape, and that the strain was proliferated through budding. No formation of sexual reproductive organs was observed in the plate 4 weeks or longer after the start of culture.

The morphological properties of the EA361 strain described above nearly matched the characteristics of *Papiliotrema flavescens* to which it was attributed by the DNA sequence analysis of the D1/D2 and ITS regions. The physiological properties of the EA071 strains are shown in Table 5.

TABLE 5

| <Saccharide fermentation test> | | | | | |
|---|---|---|---|---|---|
| Glucose | − | | | | |
| <Carbon source assimilation test> | | | | | |
| Glucose | + | Cellobiose | + | D-mannitol | + |
| Galactose | + | Salicin | + | Galactitol (dulcitol) | + |
| L-sorbose | − | Melibiose | + | Inositol | W |
| D-glucosamine | − | Lactose | + | 2-keto-D-gluconate | + |
| D-ribose | + | Raffinose | + | D-gluconate | + |
| D-xylose | + | Melezitose | + | D-glucuronate | + |
| L-arabinose | + | Inulin | + | DL-lactate | L |
| D-arabinose | + | Water soluble starch | + | Succinate | W |
| L-rhamnose | + | Glycerol | L | Methanol | − |
| Sucrose | + | Erythritol | D | Ethanol | + |
| Maltose | + | Ribitol (adonitol) | + | N-acetyl-D-glucosamine | − |
| Trehalose | + | D-glucitol (sorbitol) | + | Hexadecane | − |
| α-Methyl-D-glucoside | + | | | | |

TABLE 5-continued

| <Nitrogen source assimilation test> | | | | | |
|---|---|---|---|---|---|
| Nitrate | – | Creatinine | – | | |
| <Resistance test> | | | | | |
| Viability at 30° C. | + | Viability at 37° C. | – | | |
| 0.01% Cycloheximide | + | 50% (w/v) D-glucose | + | 10% NaCl/5% glucose | – |
| <Vitamin requirement test> | | | | | |
| Vitamin-free medium | + | | | | |

Through the measurements of the molecular phylogenetic position and physiological properties as well as the ergothioneine production, the EA361 strain was determined to be a novel microorganism attributed to *Papiliotrema flavescens*.

(11) Molecular Phylogenetic Position and Physiological Properties of EA702 Strain For the base sequences of the 26S rDNA-D1/D2 regions and ITS-5.8 rDNA in the EA702 strain, homology search by BLAST was performed across the International Nucleotide Sequence Databases. As a result, the base sequences exhibited from 99.3 to 100% homology with a plurality of base sequences of *Trichosporon porosum* (current name: *Apiotrichum porosum*) as one type of basidiomycetous yeast. In the molecular phylogenetic tree analyzed based on the obtained base sequences, the EA702 strain was included in the phyletic group composed of the genus *Trichosporon* (*Apiotrichum*). Then, the strain showed the same molecular phylogenetic position as that of *Trichosporon porosum* (current name: *Apiotrichum porosum*) CBS2040$^T$.

The EA702 strain was cultured on a YM agar plate medium at 27° C. for 7 days, and the colonies formed were observed. The shape of the margin of the colonies was filamentous. The raised state of the colonies was flat at the margin and raised at the center. The shape of the surface of the colonies was wrinkled. The colonies were dull. Furthermore, the colonies were wet to slightly dry, and white to white cream-colored.

Further, the EA702 strain was cultured on a YM agar plate medium at 27° C. for 7 days, and then the cell morphological properties thereof were also observed. It was seen that the nutritive cells were oval to ovoid in shape, and that the strain was proliferated through budding. In addition, the strain was proliferated through lateral budding, together with the hyphae elongation. No formation of sexual reproductive organs was observed in the plate 4 weeks or longer after the start of culture.

The morphological properties of the EA702 strain described above nearly matched the characteristics of *Apiotrichum porosum* to which it was attributed by the DNA sequence analysis of the D1/D2 and ITS regions. The physiological properties of the EA702 strains are shown in Table 6.

TABLE 6

| <Saccharide fermentation test> | | | | | |
|---|---|---|---|---|---|
| Glucose | – | | | | |
| <Carbon source assimilation test> | | | | | |
| Glucose | + | α-Methyl-D-glucoside | + | Xylitol | + |
| Galactose | + | Cellobiose | + | D-glucitol (sorbitol) | + |
| L-sorbose | + | Salicin | + | D-mannitol | + |
| D-glucosamine | + | Melibiose | + | Galactitol (dulcitol) | L |
| D-ribose | + | Lactose | + | Inositol | + |
| D-xylose | + | Raffinose | + | D-gluconate | + |
| L-arabinose | + | Melezitose | + | DL-lactate | + |
| D-arabinose | + | Inulin | + | Succinate | L |
| L-rhamnose | + | Water soluble starch | + | Citrate | L |
| Sucrose | + | Glycerol | + | Methanol | – |
| Maltose | + | Erythritol | + | Ethanol | + |
| Trehalose | + | Ribitol (adonitol) | + | | |
| <Nitrogen source assimilation test> | | | | | |
| Nitrate | – | Nitrite | + | Ethylamine | + |
| L-lysine | + | Creatinine | | | |
| <Resistance test> | | | | | |
| Viability at 25° C. | + | Viability at 30° C. | | | |
| Viability at 40° C. | – | 0.01% Cycloheximide | – | Viability at 37° C. | – |

TABLE 6-continued

<Vitamin requirement test>

| Vitamin-free medium | + | | + | 50% (w/v) D-glucose | + |

Through the measurements of the molecular phylogenetic position and physiological properties as well as the ergothioneine production, the EA702 strain was determined to be a novel microorganism attributed to *Papiliotrema flavescens*.

INDUSTRIAL APPLICABILITY

The microorganisms of the present invention have high ergothioneine production and can be used in the fields of health, beauty, and the like.

ACCESSION NUMBER

NITE BP-03051
NITE BP-03052
NITE BP-03053
NITE BP-03054

The invention claimed is:

1. A culture containing ergothioneine obtained by a microorganism belonging to *Dirkmeia churashimaensis* (Accession No. NITE BP-03054), a microorganism belonging to *Papiliotrema flavescens* (Accession No. NITE BP-03051), a microorganism belonging to *Papiliotrema flavescens* (Accession No. NITE BP-03052), or a microorganism belonging to *Apiotrichum porosum* (Accession No. NITE BP-03053).

2. A method for producing ergothioneine, comprising culturing the microorganism described in claim 1 to obtain a culture containing ergothioneine.

* * * * *